(12) United States Patent
Kabbash et al.

(10) Patent No.: US 11,998,801 B2
(45) Date of Patent: Jun. 4, 2024

(54) SYSTEMS AND METHODS FOR VERIFYING PHYSICAL ACTIVITIES OF USERS

(71) Applicant: The Dandy Horse, Inc., New York, NY (US)

(72) Inventors: Mark Kabbash, New York, NY (US); Luke Kabbash, New York, NY (US); Javier Richard Cook, Shrewsbury, NJ (US)

(73) Assignee: The Dandy Horse, Inc., New York, NY (US)

( * ) Notice: Subject to any disclaimer, the term of this patent is extended or adjusted under 35 U.S.C. 154(b) by 0 days.

(21) Appl. No.: 17/110,500

(22) Filed: Dec. 3, 2020

(65) Prior Publication Data
US 2021/0170232 A1    Jun. 10, 2021

Related U.S. Application Data

(60) Provisional application No. 62/943,598, filed on Dec. 4, 2019.

(51) Int. Cl.
A63B 24/00 (2006.01)

(52) U.S. Cl.
CPC ...... *A63B 24/0059* (2013.01); *A63B 24/0006* (2013.01); *A63B 24/0021* (2013.01); *A63B 24/0062* (2013.01); *A63B 2024/0012* (2013.01)

(58) Field of Classification Search
CPC ........ A63B 24/0021; A63B 2024/0025; A63B 2024/0056; A63B 24/062; A63B 2024/0065; A63B 2024/0068; A63B 2024/0071; A63B 24/0024
USPC .......................................................... 482/8
See application file for complete search history.

(56) References Cited

U.S. PATENT DOCUMENTS

| 6,050,924 A * | 4/2000 | Shea ................... | A63B 71/0697 482/57 |
| 7,056,265 B1 * | 6/2006 | Shea ................... | A63B 71/0622 482/8 |
| 7,063,643 B2 * | 6/2006 | Arai ...................... | A63B 24/00 482/8 |
| 7,643,895 B2 * | 1/2010 | Gupta ................... | A43B 3/0005 700/94 |
| 7,670,263 B2 * | 3/2010 | Ellis ..................... | A61B 5/0024 482/8 |
| 8,332,275 B2 * | 12/2012 | Poon ................... | G06Q 30/0641 705/26.1 |

(Continued)

FOREIGN PATENT DOCUMENTS

| CA | 2845037 A1 | 2/2013 |
| WO | 2010001318 A1 | 1/2010 |

OTHER PUBLICATIONS

European Search Report from related European Patent Application No. 2021145.8 dated Mar. 2, 2021.

*Primary Examiner* — Alvin A Hunter
(74) *Attorney, Agent, or Firm* — McCarter & English, LLP; David R. Burns

(57) ABSTRACT

Systems and methods are described for verifying physical activities of users. The systems and methods can include tags having tag identifiers, where the tags are affixed to articles of manufacture to be worn or used by the user during physical activity. The tag identifiers can be associated with the articles and can be used by the system and methods for verifying the physical activities of the user via one or more verification procedures.

20 Claims, 8 Drawing Sheets

(56) References Cited

U.S. PATENT DOCUMENTS

| | | | |
|---|---|---|---|
| 8,821,351 B2* | 9/2014 | Abuelsaad | G16H 20/30 |
| | | | 482/8 |
| 9,308,417 B2* | 4/2016 | Grundy | A63B 21/4035 |
| 9,619,639 B2 | 4/2017 | Donenfeld | |
| 9,636,048 B2* | 5/2017 | Beckman | A61B 5/4833 |
| 10,327,481 B2* | 6/2019 | Martikka | H04Q 9/00 |
| 10,878,952 B1* | 12/2020 | Patel | A63B 21/0726 |
| 11,013,958 B2* | 5/2021 | Bastide | A63B 24/0062 |
| 2017/0216667 A1 | 8/2017 | Garvey et al. | |

* cited by examiner

SYSTEMS AND METHODS FOR VERIFYING PHYSICAL ACTIVITIES OF USERS

RELATED APPLICATIONS

The present application claims priority to and the benefit of U.S. Provisional Application No. 62/943,598, filed on Dec. 4, 2019, which is incorporated by reference herein in its entirety.

BACKGROUND

Historically charities fundraising bicycle rides are based on the rider committing to the task of raising a minimum amount of money. This is done by asking friends and family members to donate a certain amount of money per mile the cyclist does during the event. Charities try to get as many as possible to participate. The charity must cover all cost associated to thousands of riders through multiple towns. Permits and large fees are the norm and required for groups greater than 50. Towns have police, ambulatory and fire departments on call, some directing traffic. There tend to be only one ride a year because the logistical hurdles are massive. Celebrities are aware of the dangers of riding in large crowds and tend to avoid the risks.

Additionally, a rider historically using applications within a phone or bicycle computers to track miles ridden. That only reflects the device traveled those miles. Those miles could have been covered on an electric bicycle or a motorized vehicle. Those stated cumulative miles are not verified as to who did them, when, and on a bicycle.

BRIEF DESCRIPTION OF DRAWINGS

Illustrative embodiments are shown by way of example in the accompanying drawings and should not be considered as a limitation of the present disclosure.

DETAILED DESCRIPTION

Described in detail herein are systems and methods for verifying physical activities of users. Embodiments of the present disclosure can enable a cyclist to reflect the miles ridden on any given day and prove that they were the sole rider. Embodiments of the present disclosure can facilitate enhanced verification procedures that can be used to facilitate charitable giving and can be used to reduce health insurance premiums for companies and their employees.

Figure 1:
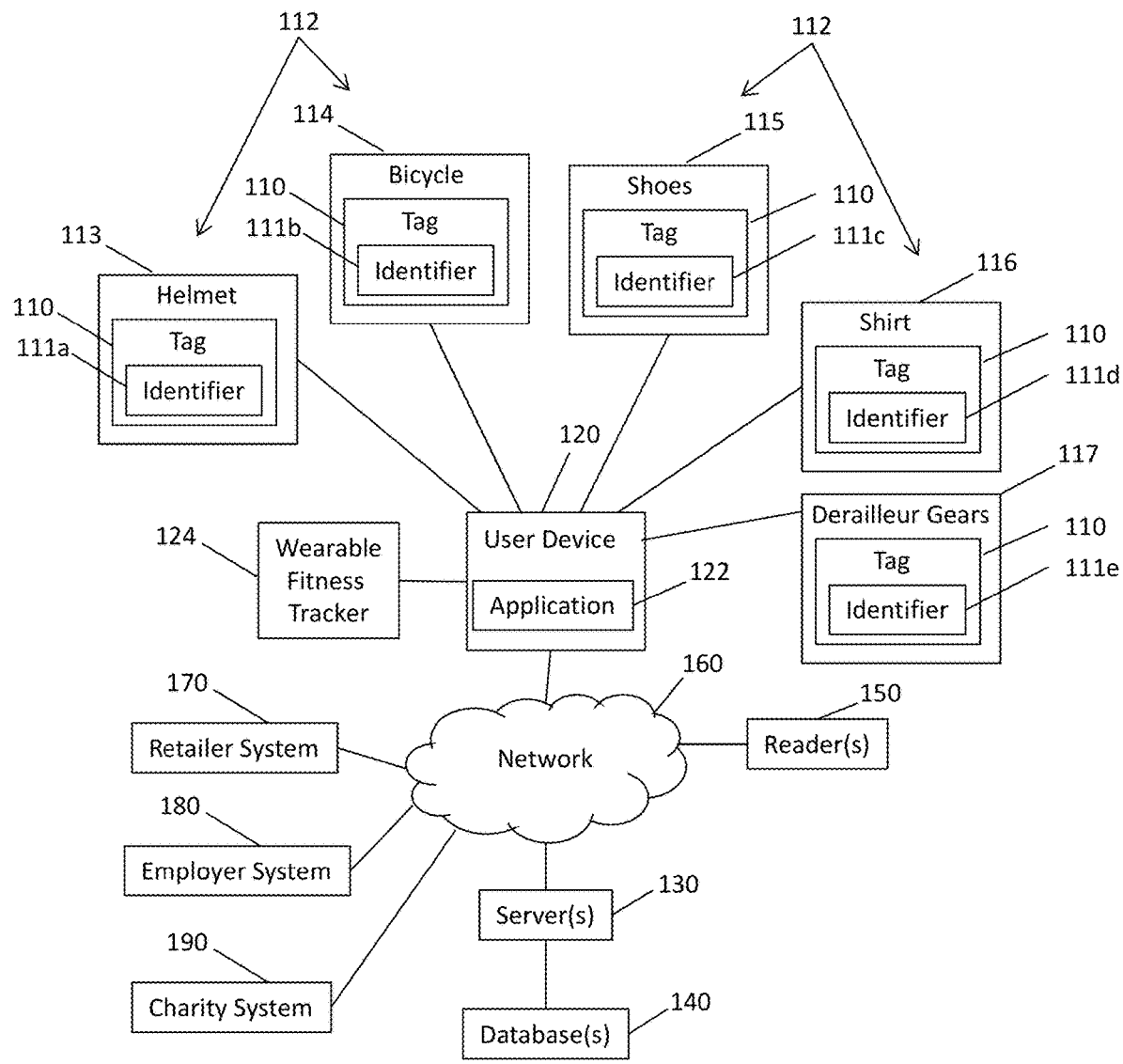
FIG. 1 is a block diagram depicting a system for verifying physical activities of users in accordance with an exemplary embodiment.

FIG. 1 is a block diagram depicting a system 100 for verifying physical activities of users in accordance with an exemplary embodiment. The system 100 can include one or more tags 110 affixed to one or more user articles of manufacture 112 (articles 112), one or more user devices 120 programmed with a verification application 122, one or more servers 130, and one or more databases 140. In some embodiments, the system 100 can include readers 150 disposed along one or more waypoints. The one or more user devices 120 can be configured and/or programmed to communicate with and/or interact with the one or more tags 110 and the one or more servers 130. For embodiments that include readers 150, the readers 150 can be configured and/or programmed by to communicate with the one or more tags 110, the one or more user devices 120, and/or the one or more servers 130.

The one or more tags 110 can be affixed to the articles 112 using one or more techniques. For example, the one or more tags 110 can include an adhesive to affix the tags 110 to the articles, can be sewn, stapled, tied, pinned, printed, and/or welded to the articles 112. In a non-limiting illustrative embodiment, the articles 112, can include a helmet 113, a bicycle frame 114, shoes 115, a shirt/jersey 116, and/or bicycle derailleur gears 117 including gear shifters, gear changers/chain-guides. More or fewer articles 112 can be used. Examples of other articles 112 to which the one or more tags can be affixed can include a card, gloves, watch, ring, shorts, bicycle wheels, seats, etc. In some embodiments, components of the bicycle can be controlled via wireless communication. For example, rather than connecting a gear shifter of the bicycle to a gear changer/chain-guide of the derailleur gears of the bicycle with one or more wires/cables, the gear shifter and gear changer/chain-guide can include electronics and can communicate wirelessly, e.g., via radiofrequency. As one example, the gear shifter and gear changer/chain-guide of the derailleur gears of the bicycle can be Bluetooth-enabled devices that allow input to the gear shifter to cause the gear shifter to send a message to the gear changer/chain-guide to change a gear of the bicycle. Such components can be utilized as tags that also include identifiers that can be used by the system 100 as tag identifiers and/or can be used by the user device 120 and the system 100 to track gear changes, times at which gears are changed, and/or locations at which gears are changed.

The one or more tags 110 can be encoded with one or more tag identifiers. As one example, the one or more tags 110 can be passive, non-electronic tags that include machine-readable elements, such as barcodes or QR codes, encoded with the tag identifiers. The passive, non-electronic tags can be read or scanned by an imaging device or optical reader to extract the tag identifiers. As another example, the one or more tags 110 can be passive electronic tags that include circuitry (e.g., a processor, memory, inductive energy harvesting circuit, transmitter, receiver, and the like) to store the tag identifiers and/or to derive power from electromagnetic radiation. The passive electronic tags can include passive radiofrequency identification (RFID) tags, passive near-field communication (NFC) tags, and the like. Power can be induced in the passive electronic tags by a radiofrequency interrogation signals from a reader (e.g., an RFID reader or NFC reader). In response to being interrogated by the reader(s), the passive electronic tags can transmit the tag identifier(s). As another example, the one or more tags 110 can be active electronic tags that include circuitry (e.g., a processor, memory, inductive circuit, transmitter, receiver, a power source, and the like) to store the tag identifiers and a power supply. The active electronic tags can include active radiofrequency identification (RFID) tags, active near-field communication (NFC) tags, Bluetooth® enabled tags and the like. In response to being interrogated by the reader(s), the active electronic tags can transmit the tag identifier(s).

The user device 120 can be a mobile phone and/or a bicycle computer configured and/or programmed with the verification application 122 to verify physical activity of a user associated with the user device 120. As one example, a user can download the verification application 122 from an application repository or marketplace and can install the verification application 122 on the user device 120 to configure and/or program the user device 120 to perform one or more operations, functions, and/or processes described herein. As another example, the verification application 122 can be install on the user device at the time of manufacture and/or can be a native application executing the on the user device 120. The verification application 122 can request access to location information of the user device 120 determined by GPS Tracking, access to security login (e.g., the method of logging into or waking to the user device 120), access to an image capture device, and/or access to a clock of the user device 120. The user device 120 (e.g., mobile phone and/or bicycle computer) can be programmed and configured to provide mapping and routing navigation to the user and/or can be programmed to track a user's operation of a bicycle e.g., by tracking a location of the user, a route of the user, miles ridden by the user, (peak, average, and/or current) velocity of the user, (peak, average, and/or current) acceleration of the user, gears used by the user, and the like.

The user device 120 can be programmed and/or configured, via the verification application 122, to verify an identity of the user during the physical activity, identify a geographic location of the user during a physical activity, a proximity of the one or more tags 110 to the user during the physical activity, and/or whether the tags 110 are present or absent during the physical activity. In exemplary embodiments, the location of the user device 120 (e.g., a longitude and latitude) can be determined using a global positioning system (GPS) receiver within the user device 120 that is in communication with a GPS satellite. In exemplary embodiments, the user device 120 can be in communication with a peripheral device 124, such as a smart watch (e.g., smart watches manufactured by Apple, Inc., Samsung, Inc., Fitbit, Inc., Garmin, Inc., etc.) and/or other wearable fitness trackers that monitors physiological parameters of a user, such as a heart rate, blood pressure, oxygen levels, hydration, and the like. The user device 120 can execute the verification application 122 to render one or more graphical user interfaces to display information associated the physical activity of the user, and event at which the physical activity is being, was, or will be performed as well as other data maintained, generated, and/or received by the one or more servers 130 and/or stored by the one or more databases 140.

In a non-limiting example embodiment, the physical activity can be riding a bicycle and the event can be to raise money for a charity (i.e., a charity ride), which can be an organized event and an unorganized event. For example, the event can be simply be the user going for a bicycle ride by himself/herself or with a group and/or can be an event organized by an entity (e.g., a non-profit, not-for-profit, and/or for-profit entity). The tag identifiers for each of the one or more tags 110 for the user can be identical such that the one or more tags 110 have the same tag identifier or can be unique such that each of the one or more tags 110 for the user has a different tag identifier. For embodiments in which the tag identifier is the same for each of the one or more tags 110, additional information may be used to distinguish the articles 112 to which the one or more tags are affixed. For embodiments in which the tag identifiers are different for each of the one or more tags 110, the articles 112 to which the one or more tags 110 are affixed can be determined based on the tag identifiers (e.g., after an association between the articles and the one or more tags 110 is made).

In exemplary embodiments, the user device 120 can be programmed and/or configured to associate the tag identifiers of each of the one or more tags 110 with a corresponding one of the articles 112 such that when the user device 120 receives a transmission from, or reads/scans, one of the tags 110, the user device 120 can determine to which of the articles 112 the one or more articles 112 are affixed. In some embodiments, the one or more tags 110 associated with a user can includes identical tag identifiers that are unique to the user such that each user can have a set of tags 110 that is unique from other users. For example, in exemplary embodiments, the tags 110 and the user device 120 can be configured to be associated with each other such that each of the tags 110 associated with the user can be recognized and/or paired with the user device 120 associated with the user via the verification application 122. During a formation or pairing process, the tag identifier of each one of the tags 110 can be received or read by the user device 120 and the user can interact with the user device 120 to identify the corresponding articles 112 to which each of the tags 110 are affixed. The user device 120 can store this information for use when it receives or reads the tag identifiers from the tags 110. For embodiments in which the tags 110 are passive, non-electronic tags, the user device can read/scan the tags 110 using an imaging device or an optical scanning device. For embodiments in which the tags 110 are passive or active electronic tags, the user device 120 can transmit and/or receive wireless transmissions including the tag identifiers from the tags 110. For embodiments in which the tags 110 use the Bluetooth® communication protocol, the tags 110 can be paired with the user device 120.

After the verification application 122 is downloaded and installed, the verification application 122 can be executed on the user device 120. For example, after the user activates the login process into a mobile phone (e.g., via facial recognition, retina scan, fingerprint detection, a swipe or gesture, a personal identification number (PIN), or voice recognition), the user can launch the verification application 122, which causes the verification application 122 to render a graphical user interface (GUI) on a display of the user device 120. Initially, the user can create a profile or account for the verification application 122, which can be maintained by the one or more servers 130 and stored in the one or more databases 140. The user can enter pertinent data/information into the GUI to create the account/profile, and a device identifier of the user device 120 can be associated with the account/profile. In exemplary embodiments, the device identifier can be a Media Access Control (MAC) address/identifier, a Wi-Fi address, a token, and/or any other suitable identifier that can be used to identify the user device. As one example, when the user creates an account with the user device 120, the one or more servers 130 can generate and/or assign a token to the user device 120. The user device 120 can store the token, which can be used by the system 100 to identify the user device 120. The data/information entered into the account/profile can include: a name of the user; an age of the user; a gender of the user; a username and password; a weight of the user; a type of (non-electric) bicycle used (e.g., brand name and/or model); a serial number of the bicycle; an image of the bicycle; an image of the serial number on the bicycle; a color of the bicycle; an employer of the user; one or more charities for which the user will raise, or is raising, money, a type of helmet (e.g., brand name and/or model), an image of the helmet on the user; a type of shoes (e.g., brand name and/or model); and/or an image of the shoes with one of the one or more tags affixed to at least one of the shoes. The user can also associate the one or more tags with the account/profile, associate the tag identifiers on or stored by the one or more tags 110 with the account/profile, and/or associate each of the one or more tags and/or tag identifiers with one of the articles 112. Before a first ride the verification application 122 can prompt the user to set up the hardware and sync the device identifier of the user device 120 with the account/profile and/or sync the tags 110.

To start an event (e.g., a ride for a charity), the verification application 122 can be activated on the user 120 and the user can be prompted to verify their identity and/or the articles 112 that have been tagged with the one or more tags 110. As an example, for embodiments in which the one or more tags are passive or active electronic tags (e.g., NFC tags, RFID tags, Bluetooth-enabled tags), the verification application 122 can activate scanner/reader, or Bluetooth transceiver of the user device 120 and can prompt the user to interrogate the tags affixed to the articles 112. When NFC tags are used, the user device 120 may be required to be placed in close proximity to each tag to be interrogated. When RFID and/or Bluetooth-enabled tags are used, the verification application 122 can control the user device 120 to autonomously interrogate the one or more tags without prompting the user and/or requiring user intervention. As another example, for embodiments in which the one or more tags 110 are passive, non-electronic tags, the user device 120 can activate an image capture device of the user device 120 and can prompt the user to capture images of the tags affixed to the articles 112. In some embodiments, different combinations of tags can be used (e.g., some tags can be NFC tags, some tags can be RFID tags, some tags can be Bluetooth-enabled tags, and/or some tags can include machine-readable elements) and/or a combination of interrogation and image capturing can be used as part of the verification process. The verification application 122 prompts the user for an image of the user with the tagged bicycle during an event. The time and location associated with the interrogations of the tags and/or the captured images can be time stamped and location stamped (e.g., the time and location can be stored as metadata associated with the interrogations and/or captured images).

In some embodiments, the user can be prompted by verification application 122, via the graphical user interface, to interrogate or capture images of the tags in a specified sequence (e.g., (1) the tag on the helmet, (2) the tag on the bicycle, (3) the tag on the shoes, and (4) the tag on the shirt/jersey). The sequence can be displayed in the graphical user interface rendered on the display of the user device 120 by the verification application 122. The sequence can be randomly generated by the verification application 122 each time the verification application prompts the user for verification.

The one or more servers 130 includes one or more computers or processors to manage data/information associated with a user's profile, account, tags, physical activities, events associated with the physical activities, and/or any other data/information associated with the user. In exemplary embodiments, the user device 120 can communicate with the one or more servers 130 via a communication network 160 to transmit and receive information. As one example, the one or more servers 130 can be programmed and/or configured to receive information about the physical activities of the user, tag identifiers from the tags 110, physiological data from the peripheral device 124, and/or user identifying information from the user device 120. The one or more servers 130 can process and/or analyze the data/information to determine whether the user has performed the physical activity, determine statistics and/or characteristics regarding the user or the physical activities performed by the user. The one or more servers can post a message on one or more social media platforms via the user's accounts on the social media platforms to notify the user's social media connections that the user plans to participate in an event or is participating in an event and providing instructions regarding how to donate.

Subsequent to determining the statistics and/or characteristics, the one or more servers 130 can transmit the statistics and/or characteristics to the user device 120 or third party systems. The user device 120 can be programmed to display the statistics and/or characteristics to the user. As another example, the one or more servers 130 can be programmed and/or configured to maintain event information, such as names, dates, and locations of events at which physical activities have, are being, or will be performed; geographic maps of courses or paths associated with the events; event participants, and/or other suitable event information. The one or more servers 130 can transmit the event information to the user device 120 upon request and/or can transmit the event information automatically. The event information can allow the user device 120 to display the names, dates, and locations of events at which physical activities have, are being, or will be performed; geographic maps of courses or paths associated with the events; event participants, and/or other suitable event information to the user. In some embodiments, the user device 120 can execute the verification application 122 to facilitate real-time navigation of the course or path of an event by the user device 120 during the event.

As an example, at the beginning of an event, after the user device 120 interrogates and/or captures the tags 110 affixed to the articles 112, the user device 12-0 can transmit this information to the one or more servers 130 with the time and location metadata. The one or more servers can validate the tag identifiers associated with the tags based on the tag identifiers stored in the profile/account created by the user and can validate the images using image recognition based on images stored in the profile/account of the user to verify the identity of the user and verify that the user is beginning an event. During the event, the verification application 122 can reconfirm the identity of the user and verify the tags to confirm that the user has covered a specified distance and/or after a specified time has elapsed since the beginning of the event. After the verification application verifies the identity of the user and the tags, the verification application 122 can prompt the rider to continue the physical activity of the event. The user can be verified during event one or more times. As one example, in some embodiments, the user can be verified at least three times for an event (e.g., a charity bicycle ride): at the start of the event; once during the event; and at an end of the event. As another example, the verification application 122 can initiate the verification process at least one time randomly every specified number of miles.

The one or more databases 140 can store information/data, as described herein. For example, the databases 140 can store information associated with users, tags 110, articles 112, and/or the one or more user devices 120. As one example, the one or more databases can store the profile/ account created by the user and can store a Media Access Control (MAC) ID of the user device 120, a name of the user, an age of the user, a gender of the user, a username and password, weight, combined miles, an image of the user, tag identifiers for the tags 110, an association between the tags 110 and the articles 112 to which they are affixed, a type of (non-electric) bicycle used (e.g., brand name and/or model), a serial number of the bicycle, an image of the bicycle, an image of the serial number on the bicycle; a color of the bicycle; an employer of the user; one or more charities for which the user will raise, or is raising, money, a type of helmet (e.g., brand name and/or model), an image of the helmet on the user; a type of shoes (e.g., brand name and/or model); and/or an image of the shoes with one of the one or more tags affixed to at least one of the shoes. The user can also associate the one or more tags with the account/profile, associate the tag identifiers on or stored by the one or more tags 110 with the account/profile, and/or associate each of the one or more tags and/or tag identifiers with one of the articles 112. The one or more databases 140 can also store a list of different charities for which donations have been collected, a total amount donated to charities, an amount of mile the user has rode, non-Employee contributions on a per-mile basis to the charities, and/or a total raised for charities by the user. For embodiments that include the readers 150, the one or more databases 140 can store information associated with the one or more readers 150 including a location of the readers 150.

In an example embodiment, the communications network 160 can be an ad hoc network, a mesh network, an intranet, an extranet, a virtual private network (VPN), a local area network (LAN), a wireless LAN (WLAN), a wide area network (WAN), a wireless wide area network (WWAN), a metropolitan area network (MAN), a portion of the Internet, a portion of the Public Switched Telephone Network (PSTN), a cellular telephone network, a wireless network, a WiFi network, a WiMax network, any other type of network, or a combination of two or more such networks.

One or more retailer systems 170 (e.g., computing systems and/or programs utilized by retailers) can interface or integrate with the system 100. For example, the retailer system 170 can execute a retailer extension application. The retailer system 170 can agree to recognize a user (e.g., a charity rider) during an event (e.g., a charity ride) by pledging 5% of a gross purchase to the charity selected by the user for the event. At the time of purchase, the user can present a wallet sized tag to the retailer. In some embodiments, a digital tag can be rendered on the display of the phone instead having a separate physical tag. The tag has previously been verified and associated with the device identifier of the user device 120 during the creation of the account/profile. The retailer system 170 scans the tag and uses retailer extension application to associate the sale with the event. The retailer system can be prompted to capture an image of the receipt and/or generate a digital receipt that the retailer system 170 transmits to the one or more server 130. The user can be prompted to capture an image of the receipt within specified amount of time of purchase using the user device 120. The image of the receipt captured by the user can be transmitted to the one or more servers 130 and the server can verify the receipt received from the retailer system 170 are the same and that the user engaged in the sale e.g., using the tag identifier of the tag, the device identifier of the user device, a device identifier or retailer code of the retailer, time metadata, and location metadata. For example, the GPS data of the user device 120 can be used to verify that the user was at the location of the retailer at the time of purchase, and the time stamp can be used to verify that the purchase occurred during the event. After verifying the purchase, the one or more servers 130 generate an update to the profile of the user regarding an amount raised for the selected charity. The one or more servers transmit a report to the retailer system 170 including the amount owed by the retailer. For example, the retailer can agree to pay five percent of the gross sale price to the selected charity, and the charity can provide a receipt of the contribution to the charity.

One or more employer systems 180 (e.g., computing systems and/or programs utilized by employers) can interface or integrate with the system 100. For example, the employer system 180 can execute an employer extension application. Employees that use the system 100 can create an account/profile for the employer. For example, an employer can participate in the system 100 can be distribute a package that includes tags, a shirt/jersey, and a link to download the verification application 122. The employee/user can register through or in association with the employer. The employer system 180 can receive statistics and characteristics from the system 100 for the employee/users. Based on the statistics and characteristics of the employee/users, the employer can receive reduced rates from insurance providers. Based on usage of the system by a user/employee, the employer can donate a percentage of the saving offered by an insurance company to the charity selected by the users/employees in the name users/employees, which can be tracked and reported to the taxing authority (e.g., the IRS).

One or more charity systems 190 (e.g., computing systems and/or programs utilized by charities) can interface or integrate with the system 100. For example, the charity system 190 can execute a charity extension application. In exemplary embodiments, the charity system 190 can interact with users, employers, and/or retailers of the system 100 that have added the charity of the charity system 190 to their profiles/accounts and/or can interact with a some, all, or none of the users, employers, retailers of the system 100. In exemplary embodiments, the charity system 190 can receive information from the one or more servers 130 of the system, such as donation statistics (e.g., how much money has been donated or pledged to the charity by users, employers, retailers, which users, employers, and/or retailers have selected the charity, a total number of miles ridden for the charity, and the like). In an exemplary embodiment, the charity system 190 can send routes to users to follow for events (e.g., organized charity rides) and/or can send user suggested routes to groups of users for to ride. The user device 120 can receive the routes and the use can select one or more of the routes via a graphical user interface of the verification application 122. If a user selects one or more of the routes sent by the charity system 190 and the user's participation has been verified by the one or more servers, the one or more servers can provide a report to the charity system 190 indicating the users and/or the number of users that selected and start or completed the route, the amount funds raised or pledge by the users, employers, and/retailers based on the users' participation, and the like.

The system 100 can integrate and/or interface with one or more other systems or applications. As one example, in some embodiments, the system 100, or portions thereof, can be integrated with and/or interface with one or more activity tracking applications such as Strava, MapMyRide, Cyclemeter. As another example, in some embodiments, the system 100, or portions thereof, can be integrated with and/or interface with one or more activity tracking devices or bicycle computers, such as Karoo manufactured by Hammerhead Navigation Inc. and/or Garmin Edge® 1030 manufactured by Garmin Ltd.

In some embodiments, the system 100, or portions thereof, can be integrated with and/or interface with one or more health insurers software or systems. The health insurer software and/or system can use the data/information from the account/profile of the user to provide incentives for performing physical activities using the system 100, such as reduced insurance premiums based on the data/information associated with the physical activity of the user that has been verified by the system 100 (e.g., if the system 100 verifies that the user has rode a bicycle for a specified number of miles a week, the insurance software or system can reduce the premium of the user by a certain percentage.

In an exemplary operation, a user downloads the verification application 122 and installs it on the user device 120 to configure and/or program the user device 120 to verify user participation in a physical activity at an event (e.g., a charity bicycle ride). The one or more tags 110 can be affixed to articles 112 and the tags can be associated with the articles to which they are affixed in an account/profile created by the user in the system 100. To start the event, the user opens the verification application 122 on the user device 120, which renders a graphical user interface (GUI) on the display of the user device 120. The GUI can request that the user select the charity to which money will be donated for the event and can prompt the user to verify themselves and the articles 112 which have been tagged by the tags 110. To verify the user, the articles 112, and the tags, the verification application 122 via the GUI can prompt the user to capture one or images of the user and/or the articles 112 with the tags 110 affixed thereto and/or can prompt the user to use the user device 120 to interrogate the tags to receive the tag identifiers. The verification application 122 can cause the user device 120 to transmit the image(s) and/or the tag identifiers to the one or more servers 130, which can query the one or more databases 140 using the device identifier of the user device 120 or other account/profile data/information and can determine whether the tag identifiers match the tag identifiers stored in the database 140 match the tag identifiers received from the user device 120 and/or user image recognition to determine whether the image(s) received match the image(s) in the database.

Upon initially verifying the user at the beginning of the event, the verification application 122 can begin recording and/or tracking the user during the event. During the event, the verification application can periodically verify the identity of the user and the tags to ensure that the user is performing the physical activity at the event. For example, in one non-limiting embodiments, the verification application 122 can periodically prompted the user to verify the proximity of a combination tags 110 by interrogating and/or capturing images of the tags. The user can be required interrogate and/or capture images of all, some, or none of the articles and/or tags 110 in a specified sequence to verify the user is performing the physical activity. Successful verification can require that the user interrogate and capture images in the order reflected in the GUI. The tag identifiers returned by the interrogations and/or the captured images can be time stamped and location stamped. This information can be transmitted to the one or more servers 130, which can use the tag identifiers and/or captured images in combination with the time and location metadata to verify the user. The one or more servers 130 can verify the user has covered a specified distance and/or a specified time has elapsed since the beginning of the event, and can prompt the user to continue the physical activity. The user can be verified at least three times: at the start of the event, once during at least a 10-mile event, and at the end of the event. The verification application 122 can also prompt the rider to perform the verification process at least one time randomly every twenty additional miles.

At any given time during the event (e.g., a charity ride), the user may have cause for a retail purchase. The user can present the wallet sized tag or digital tag to the participating retailer system, and the retailer system 170 can interrogate or capture an image of the tag to associate the sale with the event. The retailer system 170 and user device 120 can each transmit a copy of the receipt to the one or more servers 130 with time and location metadata and the tag identifier from the tag. The one or more servers can verify the device identifier of the user device 120 and a device identifier of the retailer system 170 and also verifies the tag identifier of the tag and the time and location information to verify that the purchase occurred during the event and was between the user and the retailer system 170.

Figure 2:
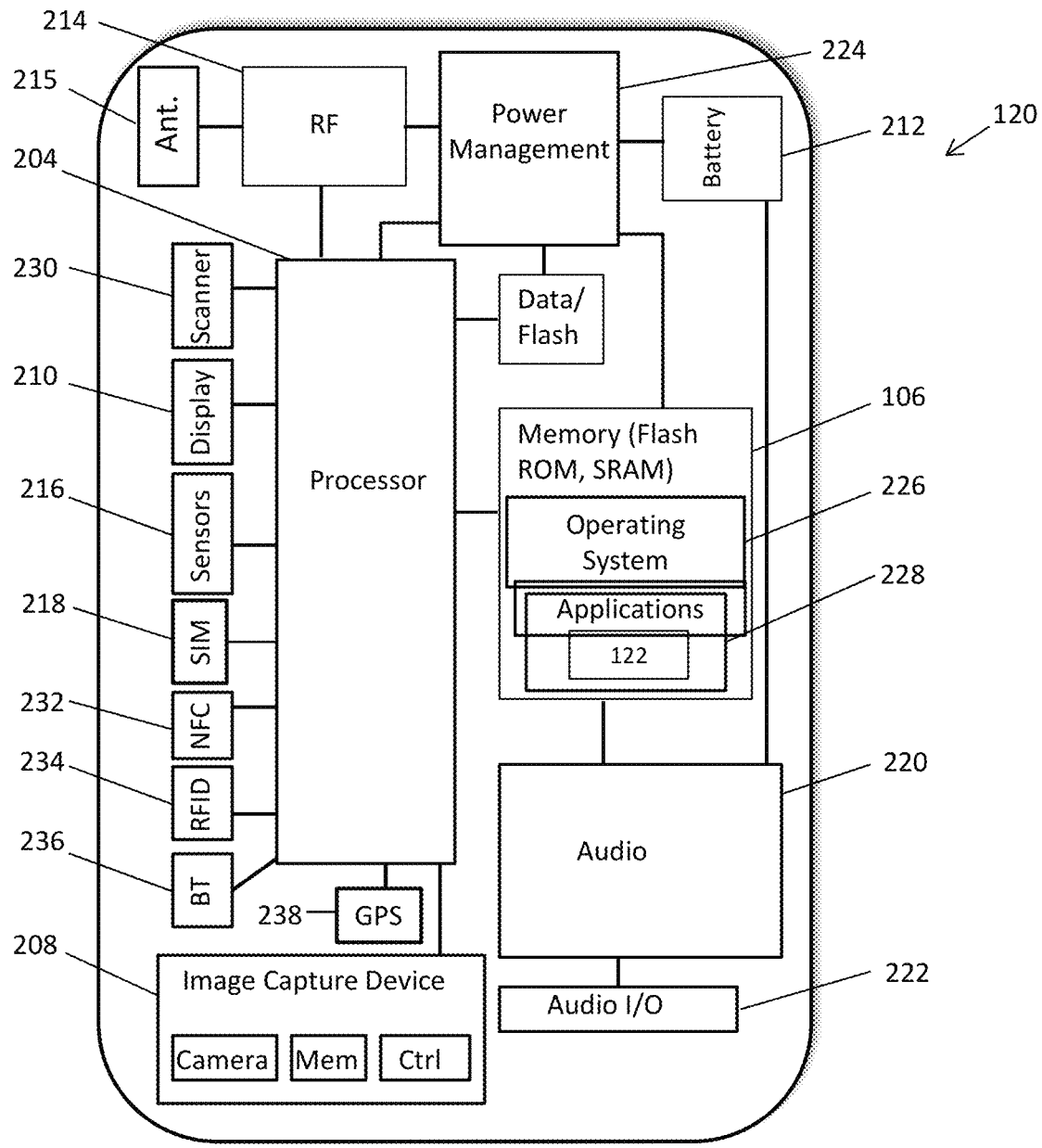
FIG. 2 depicts a mobile device in accordance with an exemplary embodiment.

FIG. 2 depicts an exemplary embodiment of the user device 120. The user device 120 can be a smartphone, tablet, personal digital assistant (PDA), handheld device, wearable device and/or any other suitable mobile device that can be programmed and/or configured and/or programmed with the verification application 122 to implement embodiments of the present disclosure. The user device 120 can include a processing device 204, memory/storage 206 in the form a non-transitory computer-readable medium, an image capture device 208, a touch-sensitive display 210, a power source 212, a radio frequency transceiver 214, an optical reader/scanner 230, a NFC reader 232, a RFID reader 234, and/or a Bluetooth transceiver 236. Some embodiments of the user device 120 can also include other common components, such as sensors 216 (e.g., accelerometers, gyroscopes), subscriber identity module (SIM) card 218, audio input/output components 220 and 222 (including e.g., one or more microphones and one or more speakers), and power management circuitry 224. The user device 120 can also include a GPS receiver 238 configured to facilitate determination of a geographic location of the user device 120.

The memory 206 can include any suitable, non-transitory computer-readable storage medium, e.g., read-only memory (ROM), erasable programmable ROM (EPROM), electrically-erasable programmable ROM (EEPROM), flash memory, and the like. In exemplary embodiments, an operating system 226 and applications 228 can be embodied as computer-readable/executable program code stored on the non-transitory computer-readable memory 206 and implemented using any suitable, high or low level computing language and/or platform, such as, e.g., Java, C, C++, C#, assembly code, machine readable language, and the like. In some embodiments, the applications 228 can include the verification application 122 executing on the user device 120. While memory is depicted as a single component those skilled in the art will recognize that the memory can be formed from multiple components and that separate non-volatile and volatile memory devices can be used.

The processing device 204 can include any suitable single- or multiple-core microprocessor of any suitable architecture that is capable of implementing and/or facilitating an operation of the user device 120. For example, a user can use the user device 120 to perform an image capture operation, capture a voice input of the user (e.g., via the microphone), interact with tags, transmit messages including a captured image and/or a voice input and receive messages from the one or more servers, display data/information including GUIs of a user interface 210, captured images, voice input transcribed as text, and the like. The processing device 204 can be programmed and/or configured to execute the operating system 226 and applications 228 to implement one or more processes and/or perform one or more operations. The processing device 204 can retrieve information/data from and store information/data to the storage device 206.

The RF transceiver 214 can be configured to transmit and/or receive wireless transmissions via an antenna 215. For example, the RF transceiver 214 can be configured to transmit data/information, such as inputs based on user interaction with the user device 120. The RF transceiver 214 can be configured to transmit and/or receive data/information having at a specified frequency and/or according to a specified sequence and/or packet arrangement.

The touch-sensitive display 210 can render user interfaces, such as graphical user interfaces to a user and in some embodiments can provide a mechanism that allows the user to interact with the GUIs. For example, a user may interact with the user device 120 through touch-sensitive display 210, which may be implemented as a liquid crystal touchscreen (or haptic) display, a light emitting diode touchscreen display, and/or any other suitable display device, which may display one or more user interfaces (e.g., GUIs) that may be provided in accordance with exemplary embodiments.

The power source 212 can be implemented as a battery or capacitive elements configured to store an electric charge and power the user device 120. In exemplary embodiments, the power source 212 can be a rechargeable power source, such as a battery or one or more capacitive elements configured to be recharged via a connection to an external power supply.

For embodiments in which the one or more tags 110 (FIG. 1) are passive, non-electronic tags that include machine-readable elements, the user device 120 can scan/read the machine-readable elements using the image capture device 208 and/or the optical scanner/reader 230. For embodiments in which the one or more tags 110 are passive or active NFC tags storing tag identifiers, the user device 120 can communicate with the one or more tags using the NFC reader 232 to receive the tag identifiers. For embodiments in which the one or more tags 110 are passive or active RFID tags storing tag identifiers, the user device 120 can communicate with the one or more tags using the RFID reader 234 to receive the tag identifiers. For embodiments in which the one or more tags 110 are Bluetooth-enabled tags storing tag identifiers, the user device 120 can communicate with the one or more tags using the Bluetooth transceiver 236 to receive the tag identifiers.

Figure 3:
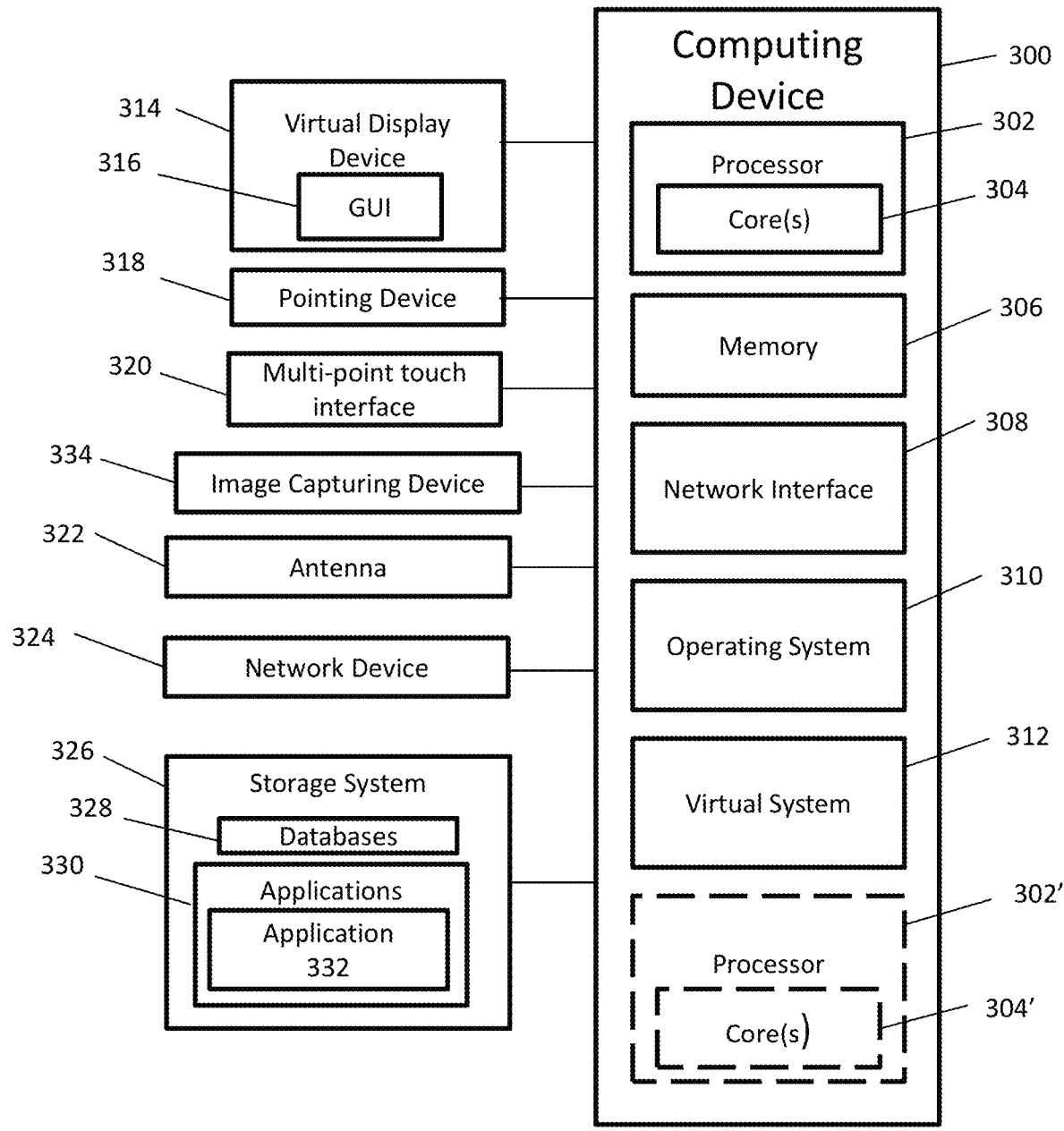
FIG. 3 depicts a computing device in accordance with an exemplary embodiment.

FIG. 3 is a block diagram of an example computing device 300 for implementing exemplary embodiments of the one or more servers described herein. The computing device 300 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 306 included in the computing device 300 may store computer-readable and computer-executable instructions or software (e.g., applications 330) for implementing exemplary operations of the computing device 300. The computing device 300 also includes configurable and/or programmable processor 302 and associated core(s) 304, and optionally, one or more additional configurable and/or programmable processor(s) 302' and associated core(s) 304' (for example, in the case of computer systems having multiple processors/cores), for executing computer-readable and computer-executable instructions or software stored in the memory 306 and other programs for implementing exemplary embodiments of the present disclosure. Processor 302 and processor(s) 302' may each be a single core processor or multiple core (304 and 304') processor. Either or both of processor 302 and processor(s) 302' may be configured to execute one or more of the instructions described in connection with computing device 300.

Virtualization may be employed in the computing device 300 so that infrastructure and resources in the computing device 300 may be shared dynamically. A virtual machine 312 may be provided to handle a process running on multiple processors so that the process appears to be using only one computing resource rather than multiple computing resources. Multiple virtual machines may also be used with one processor.

Memory 306 may include a computer system memory or random access memory, such as DRAM, SRAM, EDO RAM, and the like. Memory 306 may include other types of memory as well, or combinations thereof.

A user may interact with the computing device 300 through a visual display device 314, such as a computer monitor, which may display one or more graphical user interfaces 316, multi touch interface 320, a pointing device 318, an image capturing device 334 and a scanner 332.

The computing device 300 may also include one or more computer storage devices 326, such as a hard-drive, CD-ROM, or other computer readable media, for storing data and computer-readable instructions and/or software that implement exemplary embodiments of the present disclosure (e.g., applications). For example, exemplary storage device 326 can include embodiments of the one or more databases 140 for storing data/information described herein. The databases 140 may be updated manually or automatically at any suitable time to add, delete, and/or update one or more data items in the databases.

The computing device 300 can include a network interface 308 configured to interface via one or more network devices 324 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 322 to facilitate wireless communication (e.g., via the network interface) between the computing device 300 and a network and/or between the computing device 300 and other computing devices. The network interface 308 may include a built-in network adapter, network interface card, PCMCIA network card, card bus network adapter, wireless network adapter, USB network adapter, modem or any other device suitable for interfacing the computing device 300 to any type of network capable of communication and performing the operations described herein.

The computing device 300 may run any operating system 310, such as versions of the Microsoft® Windows® operating systems, Apache HTTP software, different releases of the Unix and Linux operating systems, versions of the MacOS® for Macintosh computers, embedded operating systems, real-time operating systems, open source operating systems, proprietary operating systems, or any other operating system capable of running on the computing device 300 and performing the operations described herein. In exemplary embodiments, the operating system 310 may be run in native mode or emulated mode. In an exemplary embodiment, the operating system 310 may be run on one or more cloud machine instances.

Figure 4:
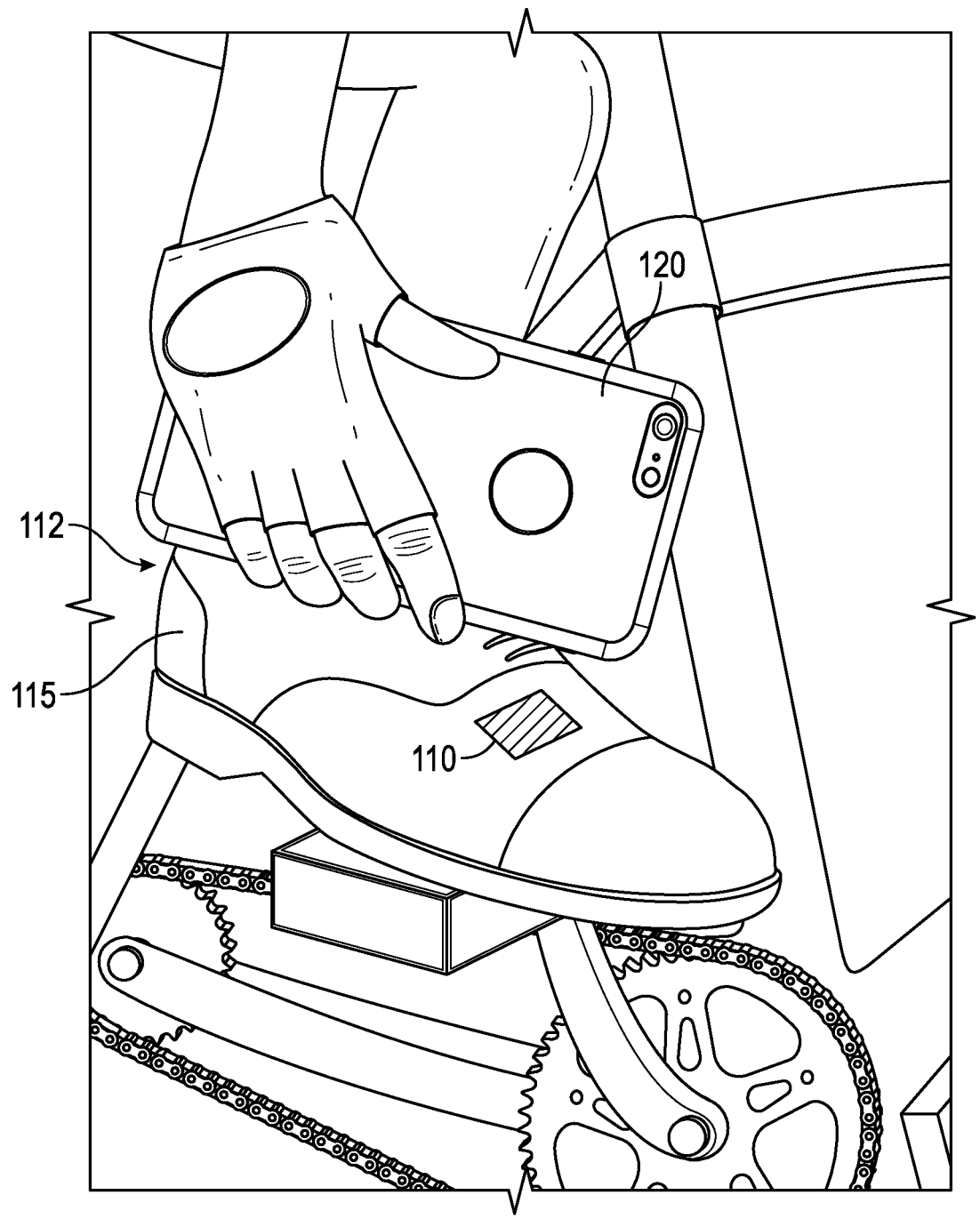
FIG. 4 illustrates a verification step of a system for verifying physical activities of users in accordance with embodiments of the present disclosure.

FIG. 4 illustrates a verification step of a system for verifying physical activities of users in accordance with embodiments of the present disclosure. As shown in FIG. 4, the user can be prompted to perform a verification process by the verification application 122 (e.g., via a GUI rendered on the display of the user device 120). At one step in the verification process, the user can be prompted to interrogate and/or capture an image of the tag affixed the article 112 (in this example, the shoe 115). The user can bring the user device 120 in proximity of the shoe 115 to scan/read and/or capture an image of the tag 110, and the tag identifier of the tag with time and location metadata can be transmitted to the one or more servers of the system 100.

Figure 5:
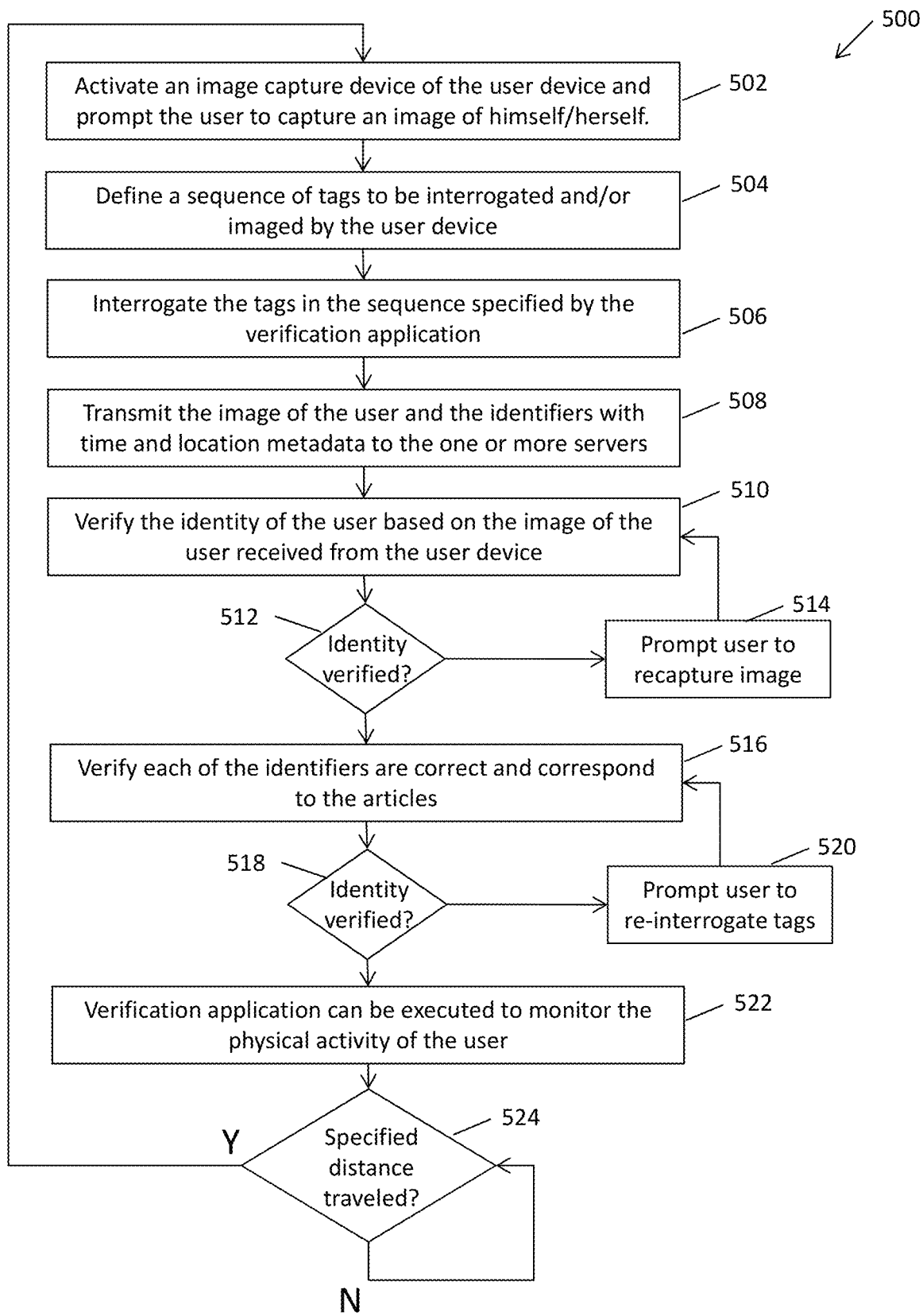
FIG. 5 is a flowchart illustrating an exemplary verification process in accordance with an exemplary embodiment.

FIG. 5 is a flowchart illustrating a verification process 500 of an embodiment of system 100 according to exemplary embodiment. As user can create an account/profile and affix tags 110 to articles 112 as described herein. When the user is ready to begin an event (e.g., a charity ride), the user can open the verification application 122 on the user device 120. The verification application renders a GUI on the display of the user device and prompts the user to verify his/her identity and to verify the tags 110 affixed to the articles 112 and the user device 120 (e.g., via the device identifier). At step 502, the verification application 122 is executed by the user device 120 to activate an image capture device of the user device 120 and prompts the user to capture an image of himself/herself. At step 504, the verification application is executed by the user device 120 to define a sequence of tags to be interrogated and/or imaged by the user device 120. At step 506, the verification application activates a reader/transceiver of the user device 120 and the user interrogates the tags in the sequence specified by the verification application using the user device. Time and location metadata is captured and associated with the image of the user and the tag identifiers received from the tags in response to being interrogated. At step 508, the image of the user and the tag identifiers with the time and location metadata are transmitted to the one or more servers 130. At step 510, the one or more servers 130 verify the identity of the user based on the image of the user received from the user device 120. For example, the one or more servers can use image recognition to compare the image of the user to a previously store image of the user to determine the identity of the user. At step 512, if the one or more servers fail to verify the identity of the user, the verification application executed by the user device prompts the user to recapture the image at step 514, and the process 500 continues are step 510. Otherwise, the process 500 proceeds to step 516, at which the one or more servers 130 can verify each of the tag identifiers are correct and correspond to the articles the user was prompted to interrogate based on a stored association between the tag identifiers and the articles. At step 518, if the one or more servers fail to verify the tag identifiers, the verification application executed by the user device prompts the user to re-interrogate the tags at step 520, and the process 500 continues at step 516. Otherwise, the process 500 proceeds to step 522, at which the user can continue the event and the verification application can be executed to monitor the physical activity of the user (e.g., a distance traveled, a current location, a time elapsed since the beginning of the physical activity). At step 524, the verification application executed by the user device 120 determines if the user traveled a specified distance (and/or if a specified time has elapsed since the beginning of the physical activity). If so, the verification process 500 repeats from step 502. If not, the verification continues to check if the user traveled the specified distance (and/or if a specified time has elapsed).

Figure 6:
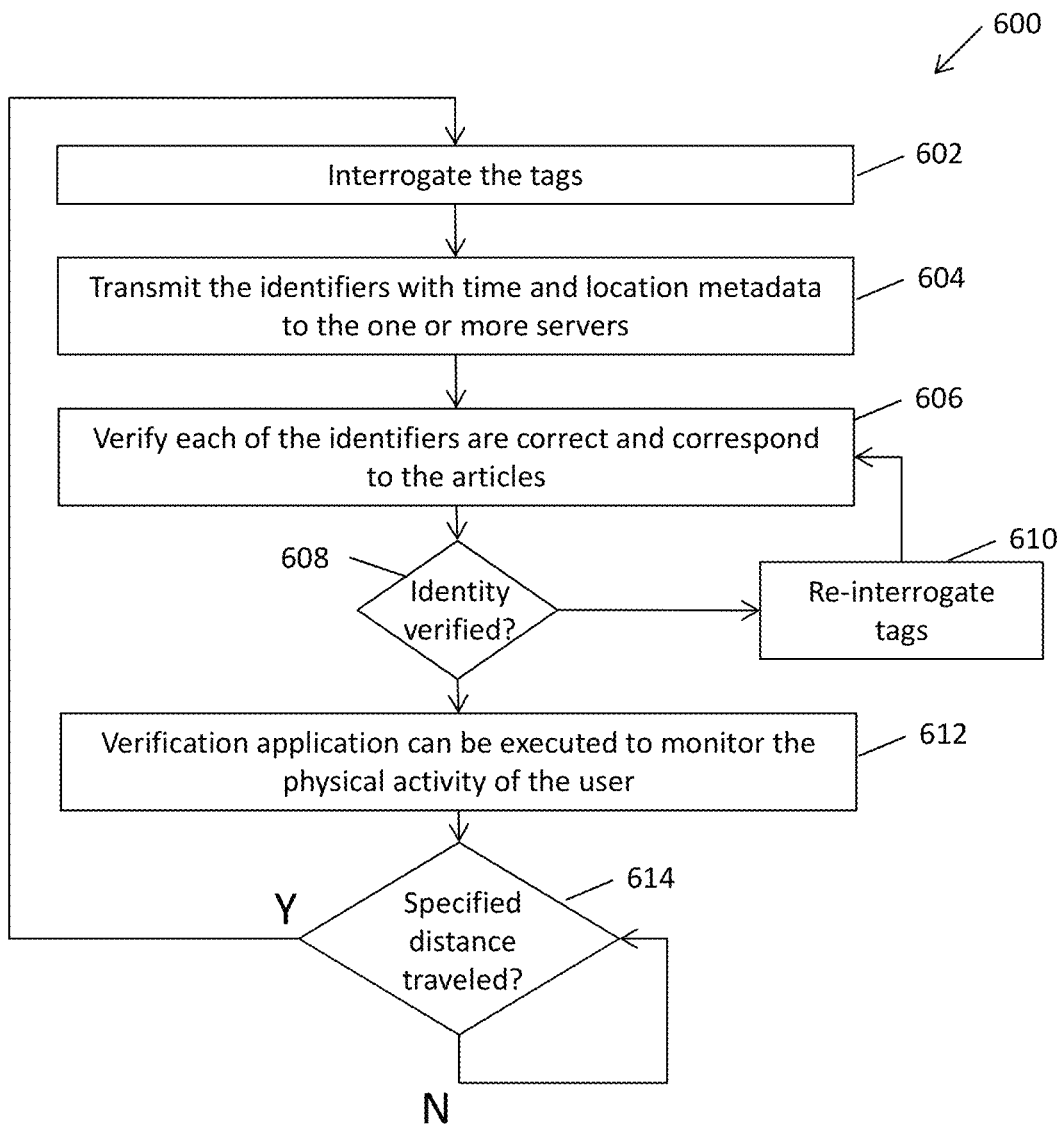
FIG. 6 is a flowchart illustrating another verification process in accordance with an exemplary embodiment.

FIG. 6 is a flowchart illustrating another verification process 600 of an embodiment of system 100 according to exemplary embodiment. As user can create an account/profile and affix tags 110 to articles 112 as described herein. When the user is ready to begin an event (e.g., a charity ride), the user can open the verification application 122 on the user device 120. At step 602, the verification application is executed by the user device 120 to activate a reader/transceiver to autonomous interrogate tags within range of the reader/transceiver. Time and location metadata is captured by the user device 120 and associated with the tag identifiers received from the tags in response to being interrogated. At step 604, the user device transmits the tag identifiers and the time and location metadata to the one or more servers 130. At step 606, the one or more servers 130 can verify each of the tag identifiers are correct and correspond to the articles of the user based on a stored association between the tag identifiers and the articles. At step 608, if the one or more servers 130 fail to verify the tag identifiers, the verification application executed by the user device autonomously re-interrogates the tags at step 610, and the process 600 continues are step 606. Otherwise, the process 600 proceeds to step 612, at which the verification application can be executed to monitor the physical activity of the user (e.g., a distance traveled, a current location, a time that has elapsed). At step 614, the verification application executed by the user device 120 determines if the user traveled a specified distance (and/or if a specified time has elapsed since the beginning of the physical activity). If so, the verification process 600 repeats from step 602. If not, the verification continues to check if the user traveled the specified distance (and/or the specified time has elapsed).

Figure 7:
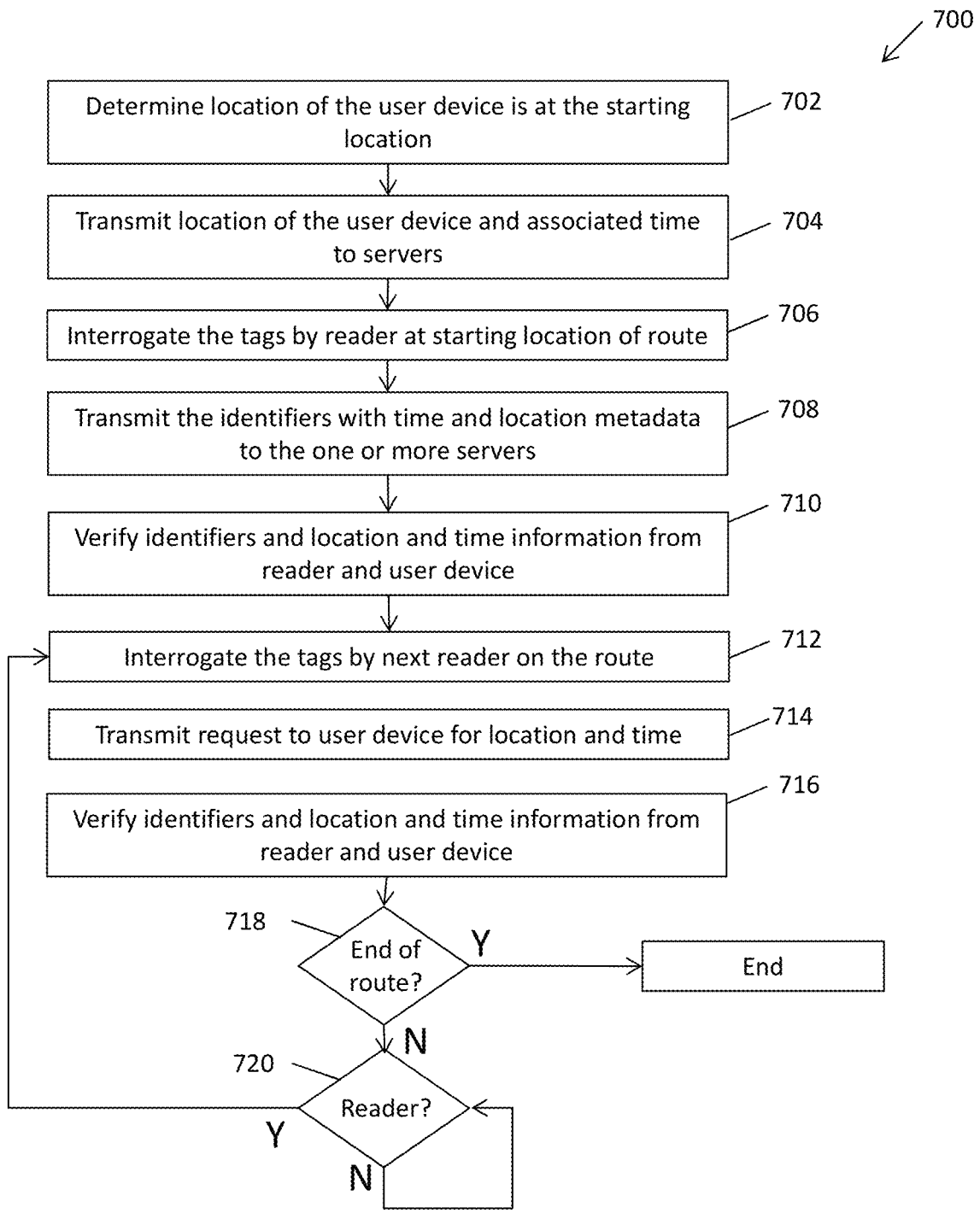
FIG. 7 is a flowchart illustrating another verification process in accordance with an exemplary embodiment.

FIG. 7 is a flowchart illustrating another verification process 700 of an embodiment of system 100 according to exemplary embodiment. As user can create an account/profile and affix tags 110 to articles 112 as described herein. When the user is ready to begin an event (e.g., a charity ride), the user can open the verification application 122 on the user device 120. The event can have a specified route and readers 150 can be disposed along the route. At step 702, the verification application is executed by the user device 120 to determine a location of the user device 120 corresponds to a starting location and a time at which the user is at the starting location. At step 704, the location and time are transmitted to the one or more servers 130. One of the readers 150 can be disposed at the starting location, and at step 706, the reader 150 at the starting location can interrogate the tags affixed to the articles of the user. Time and location metadata is captured by the reader and associated with the tag identifiers received from the tags in response to being interrogated. At step 708, the reader 150 at the starting location can transmit the tag identifiers and the time and location metadata to the one or more servers 130. At step 710, the one or more servers 130 can verify each of the tag identifiers are correct and correspond to the articles of the user based on a stored association between the tag identifiers and the articles and that the user device is co-located with the tags. As the user travels the route, the user can pass the next one of the readers 150 on the route, which can interrogate the tags 110 at step 712 and transmit a device identifier and the tag identifiers and time and location metadata to the one or more servers 130. In response to the one or more servers 130 receiving the identifiers, at step 714, the one or more servers 130 can transmit a request for location and time information from the verification application executing the user device 120. At step 716, the location and time information can be compared to the location and time information received from the next one of the readers and can verify the tag identifiers and device identifier to verify that the user has reached the next one of the readers 150. At step 718, the one or more servers determine whether the end of the route has been reached. If so, the process 700 ends. If not, the one or more servers determine whether the user reaches another one of the readers of the route (step 720). If so, and the process 700 repeats from 712. Otherwise the process waits until the next reader 150 along the route is reached.

Figure 8:
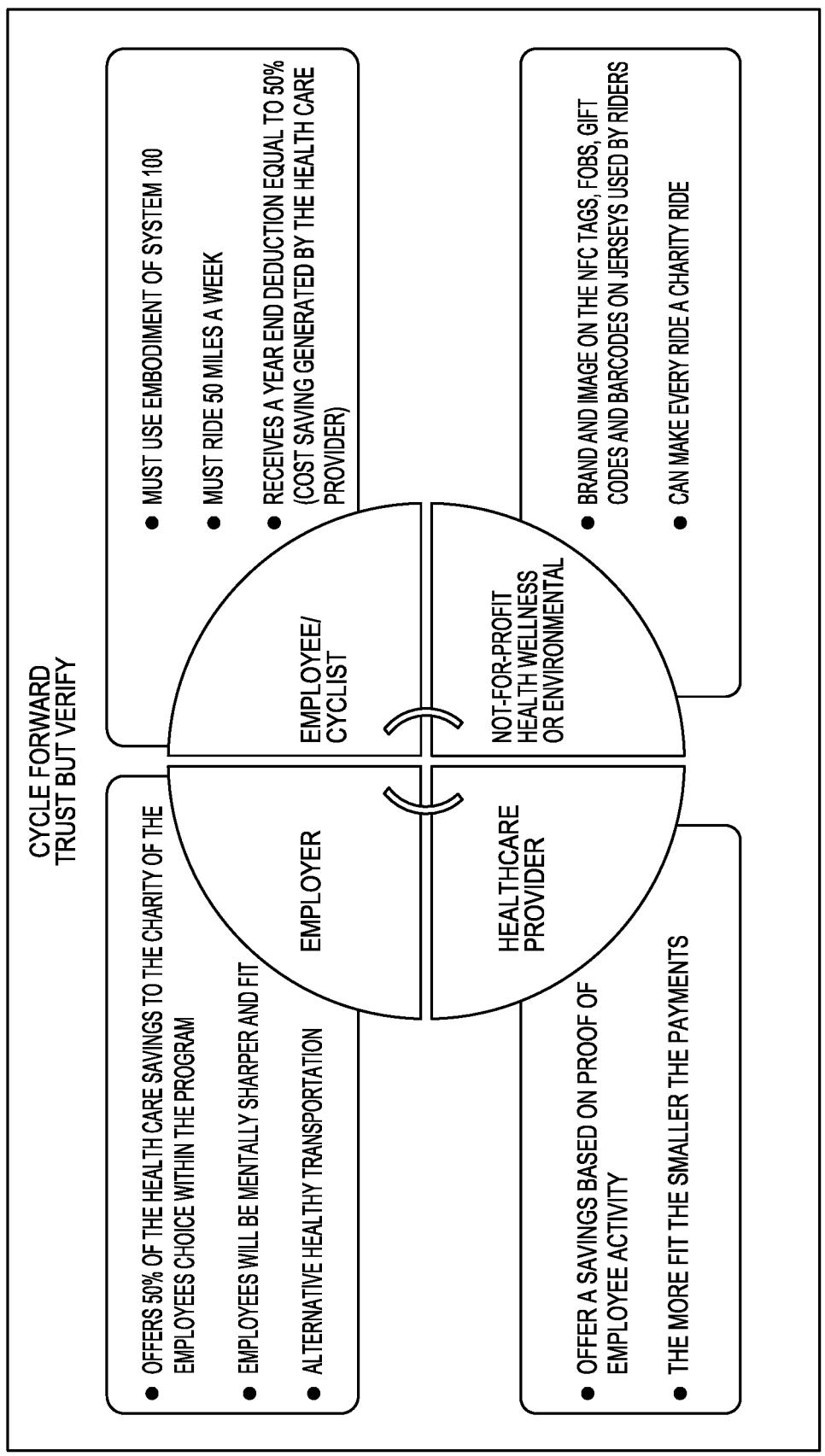
FIG. 8 is an exemplary diagram illustrating an ecosystem for a system for verifying physical activities of users in accordance with embodiments of the present disclosure.

FIG. 8 is an exemplary diagram illustrating an ecosystem 800 for an embodiment of the system 100 for verifying physical activities of users in accordance with embodiments of the present disclosure. As shown in FIG. 8, employers, employees, charities, and healthcare providers (insurers) can form an ecosystem for the embodiments of the system 100, where the employers can offer its employees an opportunity to use the system 100 to promote charitable giving and physical activities. The charities can benefit from the system by receiving donations for charity rides by a solo rider or group of riders that are not necessary participating in a charity event organized by the charity. The healthcare providers can use the data from the system to make informed decisions regarding health insurance rates and package to offer to the employer, where reduced fees can be recognized by the employer based on the verified physical activities of the employees. The employer can use some of the saving to reduce the cost of health insurance for its employees and to donate to charities in the name of its employees.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a multiple system elements, device components or method steps, those elements, components or steps may be replaced with a single element, component or step. Likewise, a single element, component or step may be replaced with multiple elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the present disclosure. Further still, other aspects, functions and advantages are also within the scope of the present disclosure.

Exemplary flowcharts are provided herein for illustrative purposes and are non-limiting examples of methods. One of ordinary skill in the art will recognize that exemplary methods may include more or fewer steps than those illustrated in the exemplary flowcharts, and that the steps in the exemplary flowcharts may be performed in a different order than the order shown in the illustrative flowcharts.

The invention claimed is:

1. A system for verifying physical activity of a user, the system comprising:
   one or more tags affixed to one or more articles of clothing, the one or more tags including tag identifiers;
   a user device programmed with a verification application, the user device programmed to:
   execute the verification application to:
     activate a verification procedure for retrieving the tag identifiers from the tags,
     define a sequence of interrogation of the tag identifiers,
     associate metadata with the tag identifiers upon retrieval, wherein the metadata includes one or more outdoor geographical locations at which the tag identifiers are retrieved, and
     associate the one or more tag identifiers with the one or more articles of clothing; and
   one or more servers in communication with the user device, the one or more servers programmed to receive the tag identifiers and the metadata and to:
     verify the physical activity of the user, and a distance traveled by the user along a route taken between each of the one or more outdoor geographical locations based on the tag identifiers and the metadata.

2. The system of claim 1, wherein the user device executes the verification application to activate the verification procedure at a beginning of the physical activity.

3. The system of claim 1, wherein the user device executes the verification application to activate the verification procedure at an end of the physical activity.

4. The system of claim 1, wherein the user device executes the verification application to activate the verification procedure during the physical activity.

5. The system of claim 4, wherein the verification procedure is activated after a specified distance traveled.

6. The system of claim 4, wherein the verification procedure is activated after a specified time has elapsed.

7. The system of claim 1, wherein the metadata includes times at which the tag identifiers are retrieved.

8. The system of claim 1, wherein the one or more tags are Near Field Communications (NFC) tags or Radio Frequency Identifier (RFID) tags, and the one or more articles of clothing include a ring.

9. The system of claim 1, wherein one or more tags are passive.

10. The system of claim 1, wherein the one or more servers are in communication with a retailer system, and
   wherein one of the tags is capable of being scanned by the retailer system to facilitate a transaction between the retailer system and the one or more servers.

11. A method of verifying physical activity of a user, the method comprising:
   executing a verification application on a user device;
   defining a sequence of interrogation of tag identifiers;
   retrieving tag identifiers from tags affixed to articles of clothing associated with the user;
   associating the tag identifiers with:
     metadata upon retrieval of the tag identifiers, wherein the metadata includes one or more outdoor geographical locations at which the tag identifiers are retrieved, and
     the articles of clothing;
   transmitting the tag identifiers and the metadata to one or more servers for verification; and
   verifying the physical activity of the user, and a distance traveled by the user along a route taken between each of the one or more outdoor geographical locations by the one or more servers based on the tag identifiers and the metadata.

12. The method of claim 11, further comprising:
activating a verification procedure at a beginning of the physical activity.

13. The method of claim 11, further comprising:
activating a verification procedure at an end of the physical activity.

14. The method of claim 11, further comprising:
activating a verification procedure during the physical activity.

15. The method of claim 14, wherein the verification procedure is activated after a specified distance traveled.

16. The method of claim 14, wherein the verification procedure is activated after a specified time has elapsed.

17. The method of claim 11, wherein the metadata includes times at which the tag identifiers are retrieved.

18. The method of claim 11, further comprising:
communicating with a retailer system via the one or more servers; and
receiving one of the tag identifiers of one of the tags by the one or more servers from the retailer system in response to the one of the tags being scanned by the retailer system; and
completing a transaction between the retailer system and the one or more servers.

19. A non-transitory computer-readable medium comprising instructions that when executed by a processing device causes the processing device to:
execute a verification application on a user device;
define a sequence of interrogation of tag identifiers;
retrieve tag identifiers from tags affixed to articles of clothing associated with the user device;
associate the tag identifiers with:
metadata upon retrieval of the tag identifiers, wherein the metadata includes one or more outdoor geographical locations at which the tag identifiers are retrieved, and
the articles of clothing;
transmit the tag identifiers and the metadata to one or more servers for verification of a physical activity, and a distance traveled by the user along a route taken between each of the one or more outdoor geographical locations by the one or more servers based on the tag identifiers and the metadata.

20. The medium of claim 19, wherein the metadata includes times at which the tag identifiers are retrieved.

* * * * *